United States Patent
Lang et al.

(10) Patent No.: US 10,012,602 B2
(45) Date of Patent: Jul. 3, 2018

(54) METHOD FOR GENERATING X-RAY IMAGE DATA, X-RAY SYSTEM AND DATA PROCESSING UNIT

(71) Applicant: SIEMENS HEALTHCARE GMBH, Erlangen (DE)

(72) Inventors: Thomas Lang, Munich (DE); Nicole Maass, Fuerth (DE); Frank Dennerlein, Forchheim (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 15/784,308

(22) Filed: Oct. 16, 2017

(65) Prior Publication Data

US 2018/0106734 A1    Apr. 19, 2018

(30) Foreign Application Priority Data

Oct. 14, 2016   (DE) .................. 10 2016 220 096

(51) Int. Cl.
*G01N 23/00*    (2006.01)
*G01N 23/046*   (2018.01)

(52) U.S. Cl.
CPC ..... *G01N 23/046* (2013.01); *G01N 2223/303* (2013.01); *G01N 2223/401* (2013.01); *G01N 2223/419* (2013.01)

(58) Field of Classification Search
CPC ... A61B 6/5205; A61B 6/5258; A61B 6/5282; A61B 6/58; A61B 6/582; A61B 6/585;
(Continued)

(56) References Cited

U.S. PATENT DOCUMENTS

| | | | |
|---|---|---|---|
| 6,639,964 B2 * | 10/2003 | Schneider | A61B 6/032 378/7 |
| 6,925,140 B2 | 8/2005 | Bruder | |
| 7,092,482 B2 * | 8/2006 | Besson | A61B 6/0414 378/37 |

FOREIGN PATENT DOCUMENTS

| | | |
|---|---|---|
| DE | 10055739 B4 | 4/2006 |
| DE | 102011006400 A1 | 10/2012 |

OTHER PUBLICATIONS

Robert G. Gould, et. al.; "Control of Scattered Radiation by Air Gap Techniques: Applications to Chest Radiography"; American Journal of Roentgenology; Sep. 1974; vol. 122; No. 1.
(Continued)

*Primary Examiner* — Jurie Yun
(74) *Attorney, Agent, or Firm* — Laurence Greenberg; Werner Stemer; Ralph Locher

(57) ABSTRACT

A mathematical scattered radiation model with a number of parameters is specified. A test object is scanned with an X-ray system to generate a first raw dataset. The test object is scanned again to generate a second raw dataset, this time with an intermediary X-ray mask having at least one X-ray transparent region and at least one X-ray non-transparent region between the X-ray source and the test object. Parameter values are determined based on the first raw dataset and on the second raw dataset, and the scattered radiation model is calibrated with the parameter values. An examination object is scanned with the X-ray system to generate a third raw dataset and the third raw dataset is processed with the calibrated scattered radiation model to generate a corrected third raw dataset. A set of X-ray image data is generated from the examination object based on the corrected third raw dataset.

17 Claims, 2 Drawing Sheets

(58) Field of Classification Search
CPC ........ G06T 11/00; G01N 23/00; G01N 23/04; G01N 23/06; G01N 23/08; G01N 23/083; G01N 23/18
USPC .................................. 378/7, 58, 62, 207, 210
See application file for complete search history.

(56) References Cited

OTHER PUBLICATIONS

A. Krol, et. al.; "Scatter Reduction in Mammography with Air Gap"; Med Phys.; Jul. 1996; pp. 1263-1270; vol. 23(7).

\* cited by examiner

METHOD FOR GENERATING X-RAY IMAGE DATA, X-RAY SYSTEM AND DATA PROCESSING UNIT

CROSS-REFERENCE TO RELATED APPLICATION

This application claims the priority, under 35 U.S.C. § 119, of German patent application DE 10 2016 220 096.8, filed Oct. 14, 2016; the prior application is herewith incorporated by reference in its entirety.

BACKGROUND OF THE INVENTION

Field of the Invention

The invention lies in the field of X-ray imaging. Specifically, the invention relates to a method for generating X-ray image data by way of an X-ray system comprising an X-ray source and an X-ray detector with a number of regularly arranged pixels. The invention also relates to an X-ray system and a data-processing unit configured to carry out a corresponding method.

Methods for generating X-ray image data, i.e., imaging methods using X-rays, generally utilize the circumstance that, on passage through an examination object, the intensity of X-rays is, on the one hand, attenuated by absorption in dependence on the material structure of the examination object and, on the other, in dependence on the length of the path through the examination object.

With this method, the additional scatter of X-rays that also occurs on interaction with materials typically also results in a significant reduction in the quality of the images that can be generated. For this reason, it is desirable to reduce the influence of the scattered X-rays, also referred to as scattered radiation, on an imaging method of this kind.

One known approach to the solution is the use of so-called collimators or scattered radiation grids with the aid of which a large part of the scattered radiation is absorbed following passage through the examination object and before any possible technical measurements and hence filtered out of the radiation field. Here, the drawback is, on the one hand, that such collimators or scattered radiation grids sometimes occupy a large amount of space and, on the other, that they also absorb some of the non-scattered X-rays, which are then no longer available for technical measurement.

Another approach provides that the technical measurement of the X-rays is performed by means of a detector at a distance far enough away from the examination object ("air gap") to ensure that the major portion of the scattered X-rays by-pass the detector due to the fact that they are propagated in a different propagation direction than the non-scattered X-rays. However, in many cases, it is not straightforwardly possible to select any desired distance between the detector and the examination object.

A further description of said approaches can, for example, be found in the following publications:

[1] American Journal of Roentgenology—September 1974, Volume 122, Number 1—"CONTROL OF SCATTERED RADIATION BY AIR GAP TECHNIQUES: APPLICATIONS TO CHEST RADIOGRAPHY" ROBERT G. GOULD, M. S. and JOHN HALE, PH.D.

[2] Med Phys. 1996 Jul; 23(7):1263-70—"Scatter reduction in mammography with air gap." Krol A1, Bassano SINCE, Chamberlain CC, Prasad SC.

[3] iCT 2012, "Scatter Correction Methods in Dimensional CT", Matthias Baer et al, Institute of Medical Physics, Friedrich-Alexander-University (FAU)

Published German patent application DE 10 2011 006 400 A1 and U.S. Pat. No. 6,925,140 B2, which corresponds to German patent DE 100 55 739 B4, are also concerned with the subject of scattered radiation, that is to say the scattering of X-rays. In both cases, approaches are used with which a scattered radiation component is determined.

SUMMARY OF THE INVENTION

It is accordingly an object of the invention to provide a method of generating X-ray image data which overcomes a variety of the heretofore-known methods and devices of this general type and to provide an advantageous method and an X-ray system and/or a data-processing unit configured to carry out a corresponding method.

With the foregoing and other objects in view there is provided, in accordance with the invention, a method of generating X-ray image data by way of an X-ray system having an X-ray source and an X-ray detector with a number of regularly arranged pixels, the method comprising:

specifying a mathematical scattered radiation model with a plurality of parameters;

scanning a test object by way of the X-ray system to generate a first raw dataset;

inserting an X-ray mask with at least one region that is transparent to X-rays and with at least one region that is non-transparent to X-rays between the X-ray source and the test object, and scanning the test object by way of the X-ray system with the X-ray mask inserted to generate a second raw dataset;

using the first raw dataset and the second raw dataset as a basis for determining parameter values for the parameters of the scattered radiation model, and calibrating the scattered radiation model with the parameters;

scanning an examination object by way of the X-ray system to generate a third raw dataset;

processing the third raw dataset with the calibrated scattered radiation model to generate a corrected third raw dataset; and using the corrected third raw dataset as a basis for generating a set of X-ray image data from the examination object.

In this context, a corresponding method is used to generate X-ray image data and is preferably adapted to industrial applications. Therefore, it is in particular used to check products or intermediate products for quality defects. In this context, the method is advantageously embodied to investigate a plurality of very similar objects in an as simple a way as possible and in a relatively short time by means of X-rays.

In this context, X-ray image data is generated by means of an X-ray system, for example by means of a computed tomography scanner comprising an X-ray source and an X-ray detector and typically a data-processing unit. Herein, the X-ray detector is preferably embodied as a so-called indirect-conversion X-ray detector and further preferably comprises a number of regularly arranged pixels which are typically arranged in rows on the one hand and columns on the other.

The method is also used for the generation of relatively high-quality X-ray image data with which unfavorable, and hence unwanted, influences from so-called scattered radiation, i.e. from the scattered X-rays described in the introduction, are reduced. To this end, the method discloses a mathematical scattered radiation model with a number of parameters with said model being based on the generation of X-ray image data and to this end being held resident in the data-processing unit, at least when this is provided.

In this context, the mathematical scattered radiation model is typically specified once, for example, when setting up the X-ray system and/or the aforementioned data-processing unit, and accordingly the scattered radiation model is, for example, part of an operating system of the aforementioned X-ray system, which is preferably only adjusted or updated in the context of maintenance work. On the other hand, in normal operation, generally only the parameter values of the parameters of the scattered radiation model are adjusted, wherein this adjustment is also preferably not performed for every examination of an object to be examined by means of the X-ray system, but typically in the context of a calibration process, which is then typically followed by the examination of a plurality of usually similar objects without any adjustment of the parameter values.

However, in each case, according to the method described here, first, a mathematical scattered radiation model is specified. Then, in the context of a calibration process, a test object is scanned by means of the X-ray system to generate a first raw dataset and the test object is also scanned a further time to generate a second raw dataset, wherein, to generate the second raw dataset, an X-ray mask with at least one region that is transparent to X-rays and with at least one region that is non-transparent to X-rays is inserted between the X-ray source and the test object in the X-ray system.

Herein, it is not in principle relevant for the method per se whether the scan without the X-ray mask or the scan with the X-ray mask is performed first and accordingly, the sequence of the method is reversed according to an alternative variant.

In this context, the X-ray mask typically has a plate-like shape and is preferably aligned parallel to the X-ray detector. Herein, the X-ray mask is used to block the propagation of X-rays in certain directions and this way to shade certain regions on the X-ray detector so that it can be assumed that only scattered X-rays are able to impact the shaded regions of the X-ray detector since the direct route from the X-ray source to the shaded regions on the X-ray detector is blocked. The use of such an X-ray mask enables the generation, using a principle that is known per se, of statistical data on the scattered radiation, wherein said statistical data is characteristic of the test object and such characteristic scattered radiation is to be described by the mathematical scattered radiation model.

On the basis of the first raw dataset, on the one hand, and the second raw dataset, on the other, parameter values for the parameters of the scattered radiation model are further determined, wherein these are used to calibrate the scattered radiation model and are hence adapted to the statistical data, which are characteristic of the test object. Herein, according to one variant, the determination of the parameter values is performed semi-automatically with the aid of an evaluation tool of the data-processing unit or fully-automatically by the data-processing unit. Hereinafter, the calibrated scattered radiation model is used for the examination of at least one examination object, i.e. an object to be examined, which although generally different from the test object, is typically similar thereto, wherein a corresponding examination object is scanned to generate a third raw dataset by means of the X-ray system. Herein, to generate the third raw dataset, the X-ray mask is removed from the beam path again. Alternatively, the examination object is also used as the test object.

The third raw dataset is then processed to generate a corrected third raw dataset by means of the calibrated scattered radiation model and, on the basis of the corrected third raw dataset, finally, a set of X-ray image data is generated from the examination object.

As mentioned above, a scattered radiation model calibrated in this way is advantageously based on not only on the examination of an examination object, but also on a plurality of examinations or scans, wherein the different examination objects are preferably similar to one another. For example, therefore, a plurality of finished components or assemblies in a batch are investigated progressively by means of the X-ray system for quality defects, wherein the same set of parameter values is used for each of these examinations since the corresponding components or assemblies are so similar to one another that it may be assumed that a very similar scattered radiation distribution occurs in each case and that this is described very effectively by the calibrated scattered radiation model with the determined set of parameter values. In this context, for each further examination object, a further raw dataset is generated by means of the X-ray system, i.e. a fourth, a fifth etc., and each further raw dataset is processed to generate an associated corrected raw dataset by means of the previously calibrated scattered radiation model. Finally, each corrected raw dataset is used as the basis for the generation of an associated set of X-ray image data from the corresponding examination object. In particular, in such a case, then preferably one of the examination objects is also used as a test object, i.e., for example, one of the finished components or one of the finished assemblies from the batch.

Further preferably, the mathematical scattered radiation model is characterized by a correction function with which a measured intensity $I(u,v)$ with a pixel of the X-ray detector with the coordinates u and v is corrected to obtain a raw dataset, wherein the thus-corrected intensity $I_K(u,v)$ is used to generate the corresponding corrected raw dataset. In this context, the corresponding corrected raw dataset is not mandatorily used immediately to generate X-ray image data, but, for example, first stored in a permanent memory. The generation of the associated set of X-ray image data is then performed as required, sometimes at a much later point in time.

According to one advantageous variant, this correction function comprises a correction term $K_s(u,v)$ describing a component of the measured intensity $I(u,v)$ to be deducted during the correction, which is induced by scattered radiation from outside the X-ray detector impacting the pixel with the coordinates u and v.

In an advantageous development, this correction term $K_S(u,v)$ is specified as a function $f(p1(G_{P2}*I)(u,v))$, wherein the function argument is specified as a product of a first parameter P1 and a convolution of a normalized 2D Gaussian function $G_{P2}(u,v)$ with the measured intensity $I(u,v)$ and wherein a second parameter P2 corresponds to the standard deviation of the 2D Gaussian functions.

Further preferably, herein, the function f is specified as a simple linear function, i.e. a function of the type $f(p1(G_{P2}*I)(u,v))=P3(p1(G_{P2}*I)(u,v))+P4$ with the parameters P3 and P4.

Also favorable is a correction function comprising a correction term $K_U(u,v)$ describing a component of the measured intensity $I(u,v)$ to be deducted during the correction, wherein said component is induced by the influence of the environment in the X-ray detector, i.e. in particular by adjacent pixels, on the pixel with the coordinates u and v. Hence, this correction term $K_U(u,v)$ describes so-called cross-talk, which occurs in particular with indirect-conversion X-ray detectors with a scintillator.

The corresponding correction term $K_U(u,v)=P1(G_{P2}*I)(u,v)$ is in this context preferably also obtained from the product of a first parameter P1 and a convolution of a normalized 2D Gaussian function $(G_{P2})(u,v)$ with the measured intensity $I(u,v)$, wherein a second parameter P2 corresponds to the standard deviation of the 2D Gaussian function.

Furthermore, the mathematical scattered radiation model, and accordingly also the correction function, is preferably kept as simple as possible and accordingly, according to one preferable embodiment, the correction function comprises precisely the above-named two correction terms $K_S(u,v)$ and $K_U(u,v)$. This then produces $I_K(u,v)=I(u,v)-K_S(u,v)-K_U(u,v)=I(u,v)-P3(p1(G_{P2}*I)(u,v))+P4-P1(G_{P2}*I)(u,v)$.

As mentioned above, in the context of the calibration of the mathematical scattered radiation model, preferably parameter values for the parameters of the scattered radiation model are determined, i.e. one set of parameter values per calibration. In this context, the number of parameter values to be determined in a set of parameter values is preferably kept as low as possible, i.e. for example fewer than 10 and preferably fewer than 6. If the scattered radiation model is obtained by the above-named correction function with the two correction terms $K_S(u,v)$ and $K_U(u,v)$, it is, for example, necessary to determine four parameter values, namely P1, P2, P3 and P4.

To determine P1, then, for example, the intensity measured during the generation of the second raw dataset with the X-ray mask $I_{mRM}$ is plotted over the intensity measured during the generation of the first raw dataset without the X-ray mask $I_{oRM}$. In this context, account is taken of all the shaded pixels, and only these, i.e. all the pixels that, when an X-ray mask is in situ, can only be impacted by scattered X-rays from outside the X-ray detector. This results in a type of point cloud with one point for each direction from which an X-ray image is taken during a scan, on the one hand, and each pixel considered, on the other. P1 is then determined as an averaged minimum of $I_{mRM}/I_{oRM}$ in the region of maximum intensity or a robust estimate of this quotient.

The parameter value for the parameter P2 is, for example, further determined in that the average is taken from different point spread functions, which can be used to describe the intensity distribution on the X-ray detector in the transitional region between a shaded region and a non-shaded region. Further preferably, the determination is also performed according to the following principle: first, the projection image $I_{oRM}$ within the regions shaded in $I_{mRM}$ is set to 0 so that an image $I_2$ is created. $I_2$ is then convoluted with the point spread function as a result of which intensities are transferred to the region that was previously set to 0. Finally, the point spread function is sought for which the greatest possible conformity between convoluted $I_2$ and $I_{mRM}$ occurs within the shaded regions. The search takes the form of a simple coordinate search.

The determination of parameters P3 and P4 is also performed, for example, on the basis on a diagram with which the measured intensity $I_{mRM}$ with an in-situ X-ray mask is plotted over an adapted intensity $I_A$, wherein the adapted intensity $I_A$ corresponds to the measured intensity $I_{oRM}$ without an in-situ X-ray mask minus the correction term $K_U$. This once again produces a point cloud, in which, to determine parameters P3 and P4, preferably a straight line is inserted that intersects the outer ends of the point cloud as interpolation points. The slope of the corresponding straight line and its point of intersection with the axis $I_A$ then produces the values for the parameters P3 or P4.

In addition, depending upon the variant and the requirements specification, the X-ray mask required for the calibration of the mathematical scattered radiation model typically comprises a plurality of regions, in particular regularly arranged and preferably distributed regularly over a surface, that are non-transparent to X-rays regions. Here, the number of corresponding regions that are non-transparent to X-rays and/or the density of the arrangement of corresponding regions typically increases with the complexity of the geometry of the examination objects, i.e. the objects to be examined, which are to be examined by means of the X-ray system and on the basis of the method described here.

Herein, the X-ray mask itself is, for example, made of a material transparent to X-rays and, to form the region that is non-transparent to X-rays, comprises recesses in which elements made of a material that is non-transparent to X-rays are inserted.

In this context, the terms non-transparent and transparent should be understood for the purpose of this application as meaning that a transparent region only absorbs X-rays to a low degree, i.e. is, for example, made of plastic or another material with a relatively low density, and that a non-transparent region absorbs X-rays to a greater degree, i.e. is, for example, made of a metal or another material with a relatively high density.

However, in this context, it is also possible to reverse the underlying principle and accordingly the X-ray mask is then made of a material that is non-transparent to X-rays and comprises a plurality of regions, in particular regularly arranged, that are transparent to X-rays or is simply embodied as a type of perforated mask. The mathematical scattered radiation model is then adapted accordingly.

In addition, the regularly arranged regions are preferably embodied as striated, rectangular or oval, i.e. for example also circular, and in the case of a rectangular embodiment, they are further preferably arranged in the style of a checkerboard pattern.

Also favorable is an embodiment of the X-ray mask with which it comprises fewer than 200, preferably fewer than 100 and in particular fewer than 50 regularly arranged regions, which are also preferably arranged uniformly distributed over an area.

The manner in which a raw dataset is generated is also typically adapted to the respective application and in particular to the complexity of the geometry of objects to be examined. In the majority of cases, in this context, for the generation of each raw dataset, i.e. during the course of a scan, a plurality of X-ray images is taken from different directions, as is usual with 3D imaging.

Preferably, in this context, to generate each raw dataset fewer than 100, further preferably fewer than 60 and in particular fewer than 40 X-ray images are taken from different directions. However, in particularly simple cases, for example, when axially symmetrical bodies, i.e. bodies with which the projection does not substantially change over different directions, or plate-like bodies are to be examined for quality defects, one single recording from one direction is also sufficient.

Other features which are considered as characteristic for the invention are set forth in the appended claims.

Although the invention is illustrated and described herein as embodied in a method for generating X-ray image data, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Figure 1:
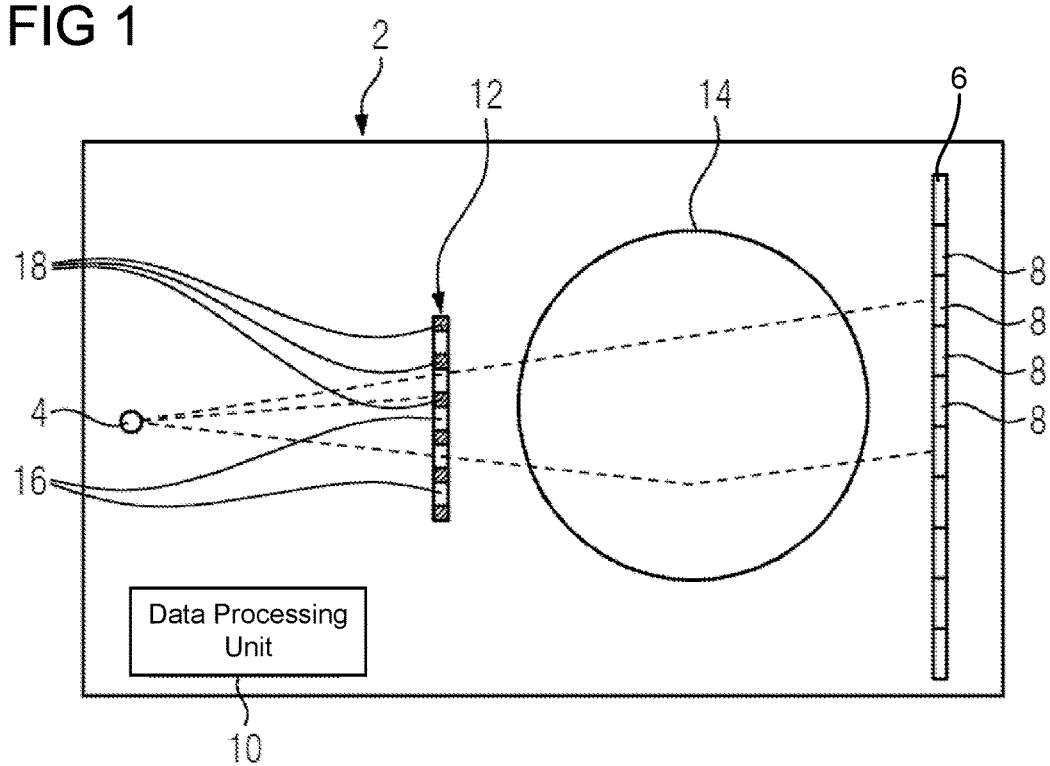
FIG. 1 shows a block diagram of an X-ray system.

Referring now to the figures of the drawing in detail and first, particularly, to FIG. 1 thereof, there is shown an exemplary X-ray system 2, which comprises an X-ray source 4, an X-ray detector 6 with a plurality of pixels 8 and a data-processing unit 10 and is embodied as a computed tomography scanner for industrial applications. Herein, the X-ray detector 6 is embodied as an indirect-conversion X-ray detector 6 the pixels 8 of which are arranged covering a wide area in rows on the one hand and columns on the other. The X-ray system 2 further comprises an X-ray mask 12, which can be moved as required into or out of the cone beam of the X-ray source 4.

In this context, if positioned in the cone beam of the X-ray source 4, this X-ray mask 12 is located upstream of the X-ray detector 6 on the one hand and a receptacle for objects 14, both test objects and examination objects, on the other, and is used to shade a number of regions on the X-ray detector 6. To this end, the X-ray mask 12 has a plate-like shape and is made of a basic material 16 that is transparent to X-rays, such as, for example, plastic, and comprises regularly arranged receptacles in which absorption elements 18 are inserted that are made of a material that is non-transparent to X-rays, for example a metal. In this context, the regular arrangement of the absorption elements 18 in the basic material 16 forms a type of checkerboard pattern.

The X-ray system 2 with this embodiment can be used to generate X-ray image data and hence X-ray images of objects to be examined, i.e. examination objects, in order to check them, for example for quality defects. In this context, the X-ray system 2 permits the generation of X-ray image data with which unfavorable unwanted influences of so-called scattered radiation, i.e. scattered X-rays, on the image quality are reduced. This reduction of unwanted influences is enabled by the use of a mathematical scattered radiation model, which is held resident in the data-processing unit 10 and taken into account during the generation of X-ray image data from objects to be examined.

The mathematical scattered radiation model is preferably a relatively simple model, which is specified as a sort of one-off, for example during the configuration of the data-processing unit 10 or in the context of the maintenance of the X-ray system 2 and/or the data-processing unit 10, and used subsequently during the operation of the X-ray system 2. In this context, the corresponding mathematical scattered radiation model comprises a number of parameters used to calibrate the mathematical scattered radiation model and which can hence be easily adapted to different objects to be examined.

In this context, in the case of industrial applications, calibration is typically performed less frequently since here there is generally a high number of very similar objects to examine. In such cases, then, a one-off calibration is performed and subsequently a plurality objects 14 examined by means of the X-ray system 2, wherein the same calibration is used as the basis for each examination, i.e. on each generation of X-ray image data from a corresponding object to be examined. For example, if a batch of a product is to be checked for quality defects by means of the X-ray system 2, a one-off calibration is performed for the batch and a set of parameter values for the parameters of the mathematical scattered radiation model is determined and subsequently this set of parameter values and the mathematical scattered radiation model calibrated therewith used as the basis for all examinations on the products in this batch.

In this context, for the calibration of the mathematical scattered radiation model, first, a test object is positioned in the X-ray system 2, wherein the test object is either one of the objects to be examined or very similar thereto. Subsequently, two scans are performed and accordingly two raw datasets generated, wherein with one of the scans, i.e. during the generation of a raw dataset, the X-ray mask 12 is used and, to this end, moved into the cone beam of the X-ray source 4.

The two raw datasets are then evaluated and these two raw datasets used as the basis for the determination of a set of parameter values. These parameter values are then used to calibrate the scattered radiation model following which X-ray image data from a plurality of objects to be examined is generated in order to examine these objects for quality defects. In this context, these objects to be examined are positioned one after the other in the X-ray system 2 and scanned by means of the X-ray system 2, wherein a set of raw data, i.e. a raw dataset, is generated for each object to be examined 14. The corresponding raw datasets from these objects to be examined are then each processed with the aid of the previously calibrated mathematical scattered radiation model and accordingly each raw dataset from the objects to be examined used as the basis for the generation of a corrected raw dataset. Finally, the corrected raw datasets are used as the basis for the generation of X-ray image data with which the influence of the scattered radiation is reduced.

In this context, depending upon the application and in particular depending upon the complexity of the geometry of the objects to be examined, a corresponding scan contains one or more X-ray images from different directions.

Figure 2:
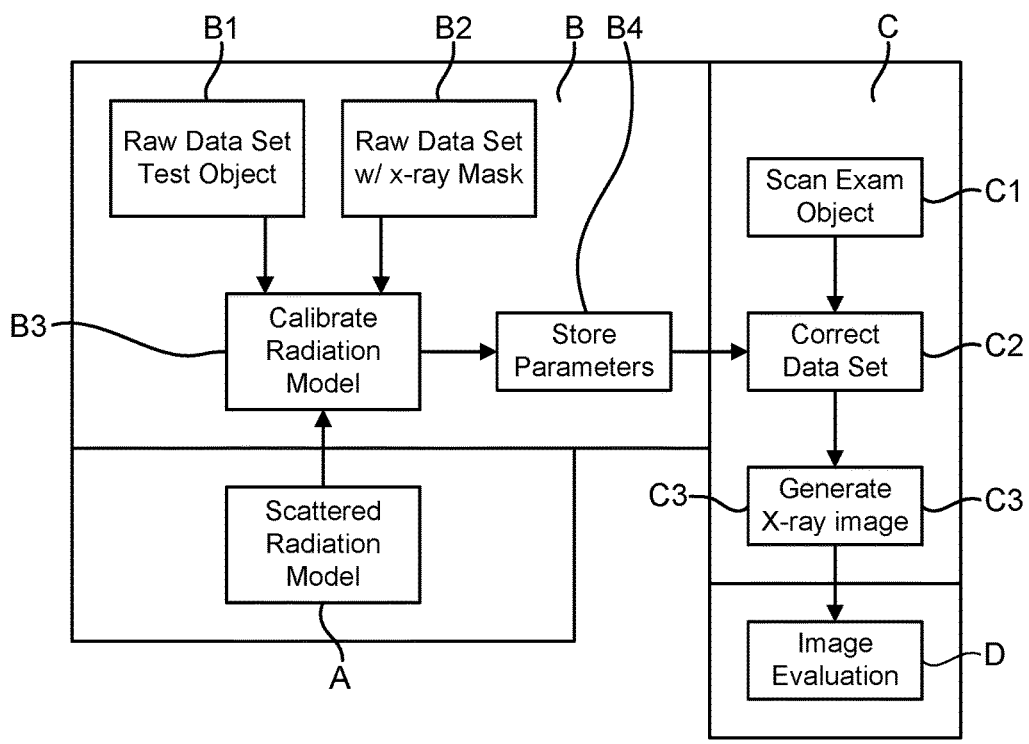
FIG. 2 shows a block diagram of method steps of a method.

The method implemented by means of the X-ray system 2 is also depicted in FIG. 2 in a type of block diagram. It includes as the primarily important components of the method A,B,C and D, i.e. the specification of a mathematical scattered radiation model A, the calibration of the mathematical scattered radiation model with the aid of a test object B, the generation of X-ray image data from at least one examination object C and optionally image post-processing or image evaluation D.

Herein, the calibration B includes at least the generation of a first raw dataset from a test object B1, the generation of a second raw dataset from the test object B2, wherein to generate the second raw dataset B2, the X-ray mask 12 is inserted between the X-ray source and the test object, the calibration of the mathematical scattered radiation model by the joint evaluation of the first raw dataset and the second raw dataset B3 and the intermediate storage of the calibrated mathematical scattered radiation model or at least the parameter values determined in the context of the calibration for the parameters of the mathematical scattered radiation model B4.

The generation of the image data C in turn includes at least the generation of a third raw dataset from an examination object C1, the processing of the third raw dataset with the aid of the calibrated scattered radiation model and the generation of a corrected third raw dataset C2 and the generation of a set of X-ray image data from the examination object on the basis of the corrected third raw dataset C3.

As mentioned above, in the context of the calibration of the mathematical scattered radiation model, parameter values are determined for the parameters of the scattered radiation model, i.e. one set of parameter values per calibration. In this exemplary embodiment, the mathematical scattered radiation model is obtained by a correction function comprising four parameters P1, P2, P3 and P4.

Figure 3:
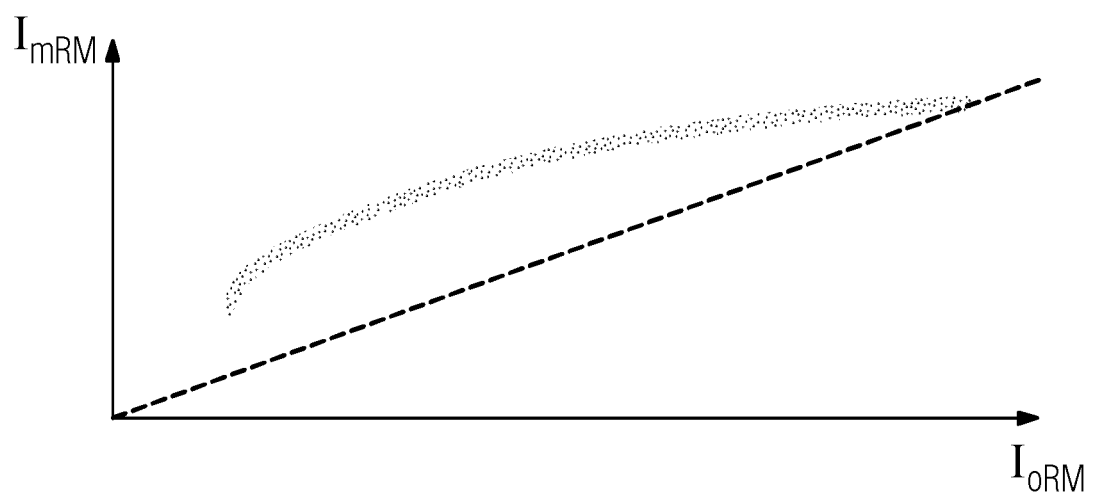
FIG. 3 shows a diagram of a first intensity distribution.

To determine P1, then the measured intensity $I_{mRM}$ with the X-ray mask 12 is then plotted over the measured intensity $I_{oRM}$ without the X-ray mask 12. This takes account of all shaded pixels 8, i.e. all pixels 8, which can only be impacted by scattered X-rays from outside the X-ray detector 6 with an in-situ X-ray mask 12. This produces a type of type point cloud with one point for each direction from which an X-ray image has been taken, on the one hand, and each pixel 8 considered on the other. The associated diagram is shown in FIG. 3. P1 is then determined as an averaged minimum of $I_{mRM}/I_{oRM}$. In FIG. 3, the dashed line has the slope P1 and intersects the point cloud in the region of maximum intensity without an in-situ X-ray mask 12.

The parameter value for the parameter P2 is, for example, further determined in that the average is obtained over different head spread functions, which can be used to describe the intensity distribution on the X-ray detector 6 in the transitional region between a shaded region and a non-shaded region.

Figure 4:
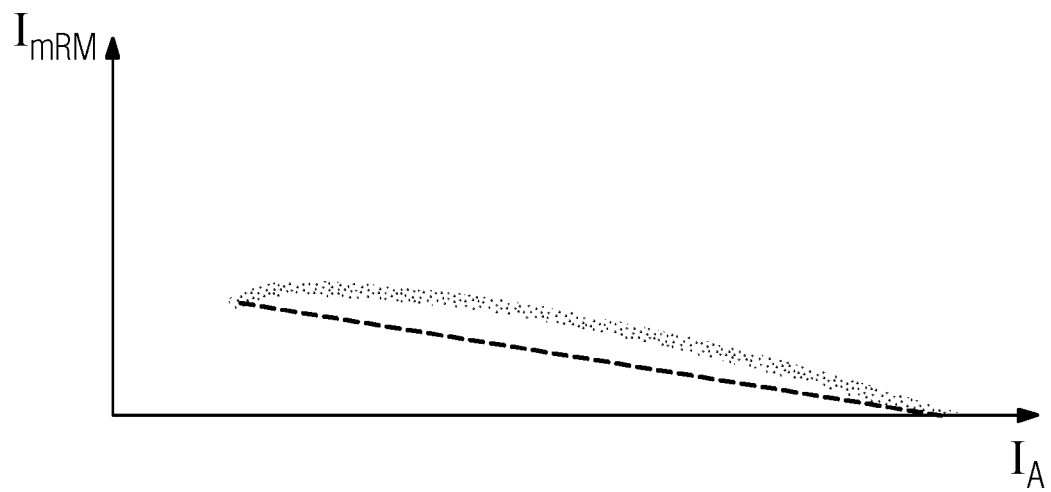
FIG. 4 shows a diagram of a second intensity distribution Corresponding parts in all figures are identified with the same reference characters throughout.

The determination of the parameters P3 and P4 is also, for example, performed on the basis of a diagram such as that shown in FIG. 4. Here, the measured intensity $I_{mRM}$ with an in-situ X-ray mask 12 is plotted over an adapted intensity $I_A$, wherein the adapted intensity $I_A$ corresponds to the measured intensity $I_{oRM}$ without an in-situ X-ray mask 12 minus the correction term $K_U(u,v)=P1(G_{P2}*I)(u,v)$, wherein u and v describe the positions of the pixels 8. This once again produces a point cloud in which, in the exemplary embodiment, to determine the parameters P3 and P4, a straight line is inserted that intersects the outer ends of the point cloud. The corresponding straight line is shows as dashed in FIG. 4. The slope of the corresponding straight line and its point of intersection with the axis $I_A$ then produces the values for the parameters P3 and P4.

The invention is not restricted to the above-described exemplary embodiment. Instead those of skill in the pertinent art may also derive other variants herefrom without departing from the subject matter of the invention. In particular, in addition, all individual features described in connection with the exemplary embodiment can also be combined with one another in another way without departing from the subject matter of the invention.

The invention claimed is:

1. A method of generating X-ray image data by way of an X-ray system having an X-ray source and an X-ray detector with a number of regularly arranged pixels, the method comprising:
    specifying a mathematical scattered radiation model with a plurality of parameters;
    scanning a test object by way of the X-ray system to generate a first raw dataset;
    inserting an X-ray mask with at least one region that is transparent to X-rays and with at least one region that is non-transparent to X-rays between the X-ray source and the test object, and scanning the test object by way of the X-ray system with the X-ray mask inserted to generate a second raw dataset;
    using the first raw dataset and the second raw dataset as a basis for determining parameter values for the parameters of the scattered radiation model, and calibrating the scattered radiation model with the parameters;
    scanning an examination object by way of the X-ray system to generate a third raw dataset;
    processing the third raw dataset with the calibrated scattered radiation model to generate a corrected third raw dataset; and
    using the corrected third raw dataset as a basis for generating a set of X-ray image data from the examination object.

2. The method according to claim 1, which comprises:
    scanning at least one further examination object by way of the X-ray system to generate a further raw dataset;
    processing each further raw dataset with the calibrated scattered radiation model to generate an associated corrected raw dataset; and
    proceeding from each corrected raw dataset, generating an associated set of X-ray image data from a respectively corresponding examination object.

3. The method according to claim 1, wherein the mathematical scattered radiation model is characterized by a correction function with which a measured intensity $I(u,v)$ with a pixel of the X-ray detector having the coordinates u and v is corrected to obtain a raw dataset and a thus-corrected intensity $I_K(u,v)$ is used to generate the corresponding raw dataset.

4. The method according to claim 3, wherein the correction function includes a correction term $K_S(u,v)$ describing a component of the measured intensity $I(u,v)$ to be deducted during the correction, the component being induced by scattered radiation from outside the X-ray detector impacting the pixel with the coordinates u and v.

5. The method according to claim 4, wherein the correction term $K_S(u,v)$ is specified as a function f, $$K_S(u,v)=f(P1(G_{P2}*I)(u,v))$$

wherein a function argument is specified as a product of a first parameter P1 and a convolution of a 2D Gaussian function $G_{P2}(u,v)$ with the measured intensity $I(u,v)$ and wherein a second parameter P2 corresponds to a standard deviation of the 2D Gaussian function.

6. The method according to claim 5, wherein the function f is a linear function.

7. The method according to claim 3, wherein the correction function includes a correction term $K_U(u,v)$ describing a component of the measured intensity $I(u,v)$ to be deducted during the correction, the component being induced by an influence of an environment in the X-ray detector on the pixel with the coordinates u and v.

8. The method according to claim 7, wherein the correction term $K_U(u,v)$ is defined as $$K_U(u,v)=P1(G_{P2}*I)(u,v),$$

being a product of a first parameter P1 and a convolution of a 2D Gaussian function $G_{P2}(u,v)$ with the measured intensity $I(u,v)$, and wherein a second parameter P2 corresponds to a standard deviation of the 2D Gaussian function.

9. The method according to claim 1, wherein the X-ray mask comprises a plurality of regularly arranged regions that are non-transparent to X-rays.

10. The method according to claim 9, wherein the regularly arranged regions have a shape selected from the group consisting of striated, rectangular and oval.

11. The method according to claim 9, wherein the X-ray mask comprises fewer than 200 regularly arranged regions.

12. The method according to claim 11, wherein the X-ray mask comprises fewer than 100 regularly arranged regions.

13. The method according to claim 1, which comprises generating each raw dataset by taking a plurality of X-ray images from different directions.

14. The method according to claim 13, which comprises generating each raw dataset by taking fewer than 100 X-ray images from different directions.

15. The method according to claim 14, which comprises generating each raw dataset by taking fewer than 60 X-ray images from different directions.

16. An X-ray system, comprising an X-ray source, an X-ray detector with a number of regularly arranged pixels and a data-processing unit, configured to carry out the method according to claim 1.

17. A data-processing unit, configured to carry out the method according to claim 1.

* * * * *